(12) United States Patent
Bainbridge et al.

(10) Patent No.: US 11,554,095 B1
(45) Date of Patent: Jan. 17, 2023

(54) MITOMYCIN-C BLADDER INSTILLATION SYRINGE KIT

(71) Applicant: Edge Pharma, LLC, Colchester, VT (US)

(72) Inventors: Melissa Lee Bainbridge, Colchester, VT (US); Brian Thomas Badgley, Waterbury, VT (US); Sara Jane Nadeau, Milton, VT (US); Steven David Kummer, Canastota, NY (US); Joseph Daniel Kummer, Fayetteville, NY (US); William Marc Chatoff, Hinesburg, VT (US)

(73) Assignee: Edge Pharma, LLC, Colchester, VT (US)

( * ) Notice: Subject to any disclaimer, the term of this patent is extended or adjusted under 35 U.S.C. 154(b) by 159 days.

(21) Appl. No.: 16/911,309

(22) Filed: Jun. 24, 2020

Related U.S. Application Data

(60) Provisional application No. 62/866,093, filed on Jun. 25, 2019, provisional application No. 62/865,850, filed on Jun. 24, 2019.

(51) Int. Cl.
*A61K 31/40* (2006.01)
*A61K 9/00* (2006.01)
*A61K 31/407* (2006.01)
*A61K 31/7068* (2006.01)
*A61K 47/02* (2006.01)
*A61K 47/10* (2017.01)

(52) U.S. Cl.
CPC .......... *A61K 9/0019* (2013.01); *A61K 31/407* (2013.01); *A61K 31/7068* (2013.01); *A61K 47/02* (2013.01); *A61K 47/10* (2013.01)

(58) Field of Classification Search
None
See application file for complete search history.

(56) References Cited

U.S. PATENT DOCUMENTS 3,660,578 A * 5/1972 Hata et al. ........... C07D 487/14
435/119
5,216,011 A * 6/1993 Paborji .................. A61K 47/10
514/410

FOREIGN PATENT DOCUMENTS

EP 0415430 * 8/1990 ............. A61K 31/40

OTHER PUBLICATIONS

Meyers et al. "Solubilization and Stability of Mitomycin C Solutions Prepared for Intravesical Administration" Drugs R D (2017) 17: 297-304 (Year: 2017).*
Sigma-Aldrich Product Information "Mitomycin C" 2pages (Year: 2008).*

* cited by examiner

*Primary Examiner* — Thane Underdahl
(74) *Attorney, Agent, or Firm* — Hodgson Russ LLP

(57) ABSTRACT

The disclosure provides compositions, methods, and devices for use in delivering Mitomycin-C(MMC), an antineoplastic chemotherapy drug often used for bladder instillations to treat bladder cancer, which degrades in both acidic and alkaline environments. The disclosure provides a solution of buffered MMC (or a different drug) in 50% propylene glycol that maintains a pH from 7.0 to 8.0 when introduced into acidic solutions (pH of 5.0) and is stable when stored at 2-8° C. for greater than 134 days. This formulation can be produced in an FDA registered 503B Outsourcing facility in a pre-filled, ready-to-administer syringe kit with pre-attached closed system transfer device and accessories required for bladder instillation.

11 Claims, 4 Drawing Sheets

MITOMYCIN-C BLADDER INSTILLATION SYRINGE KIT

CROSS-REFERENCE TO RELATED APPLICATIONS

This application claims priority to U.S. provisional patent application No. 62/865,850, filed Jun. 24, 2019, and U.S. provisional patent application No. 62/866,093, filed Jun. 25, 2019, both titled, "MITOMYCIN-C BLADDER INSTILLATION SYRINGE KIT," the entire disclosures of each of which are incorporated herein by reference.

FIELD OF THE INVENTION

This invention relates to Mitomycin-C, and in particular to the formulation and packaging of a pre-filled, ready-to-administer Mitomycin-C bladder instillation syringe kit.

BACKGROUND

The compounding and administration of hazardous pharmaceuticals, in particular chemotherapy drugs, poses significant exposure risks to health care providers. Although some organizations have appropriate USP<800> level preparations and handling facilities, equipment, and training, the vast majority of hospitals, surgery centers, and clinics will find it extremely difficult to compound chemotherapy in compliance with regulations. FDA approved drugs and devices exist that facilitate compounding and administration of hazardous drugs; however, once outsourcing is necessary, drug stability and proper packaging do not exist for Mitomycin-C. There is an ongoing and unmet need for prefilled syringe kits that contain Mitomycin-C or Gemcitabine. This need extends to a lack of available closed system transfer devices suitable for production in a 503B Outsourcing facility. There is also a need for a stable Mitomycin-C formulation appropriate for intravesical bladder instillation. The present disclosure is pertinent to these and related needs.

SUMMARY

The present disclosure provides, in various embodiments, a Mitomycin-C formulation comprising: 0.9 mg/mL to 1.2 mg/mL (0.09% and 0.12% weight/volume) Mitomycin-C; 300 mg/mL to 550 mg/mL (30% to 55% weight/volume) propylene glycol; and 0.1 mg/mL to 10 mg/mL (0.01% and 1.0% weight/volume) sodium phosphate buffer. The formulation may be used for injection or irrigation.

In embodiments, the sodium phosphate buffer comprises a combination of sodium phosphate dibasic heptahydrate and sodium phosphate monobasic anhydrous.

In embodiments, in a Mitomycin-C formulation of the disclosure, the sodium phosphate dibasic heptahydrate has a concentration that is 0.0862 mg/mL to 8.87 mg/mL (0.00862% and 0.887% weight/volume).

In embodiments, in the Mitomycin-C formulation, the sodium phosphate monobasic anhydrous has a concentration of 0.0138 mg/mL to 1.42 mg/mL (0.00138% to 0.142% weight/volume).

In embodiments, in the Mitomycin-C formulation, the sodium phosphate dibasic heptahydrate has a concentration that is 0.0862 mg/mL to 8.87 mg/mL (0.00862% to 0.887% weight/volume) and/or the sodium phosphate monobasic anhydrous has a concentration that is 0.0138 mg/mL to 1.42 mg/mL (0.00138% to 0.142% weight/volume).

In embodiments, a kit or device of this disclosure comprises approximately or precisely a formulation that comprises or consists of 40 ml of liquid volume with 40 mgs of Mitomycin-C. Thus, in embodiments, a formulation that comprises 1/mg/ml of Mitomycin-C is provided. In embodiments, for any weight/volume value described herein, the balance of the formulation comprises or consists of sterile water.

In another aspect, the disclosure provides a bladder instillation syringe kit comprising: a syringe; a closed system transfer device connected to the syringe as described herein and depicted in the figures; and a Mitomycin-C formulation as described above. The syringe kit may also be considered a device. The syringe kit may also comprise sterile water for injection or irrigation. The syringe kit may include a sodium phosphate buffer, which may comprise a combination of sodium phosphate dibasic heptahydrate and sodium phosphate monobasic anhydrous, as described above.

In embodiments, any formulation, device, or kit, or combination thereof, may be produced in a 503B Outsourcing Facility.

The disclosure comprises intravesical bladder instillation of any formulation described herein, using any device or kit described herein. In embodiments, the formulation is instilled into the bladder of a human in need thereof, or a non-human mammal in need thereof. In embodiments, the individual is in need of treatment for bladder cancer.

BRIEF DESCRIPTION OF THE DRAWINGS

For a fuller understanding of the nature and objects of the disclosure, reference should be made to the following detailed description taken in conjunction with the accompanying drawings.

DETAILED DESCRIPTION OF THE INVENTION

Figure 1:
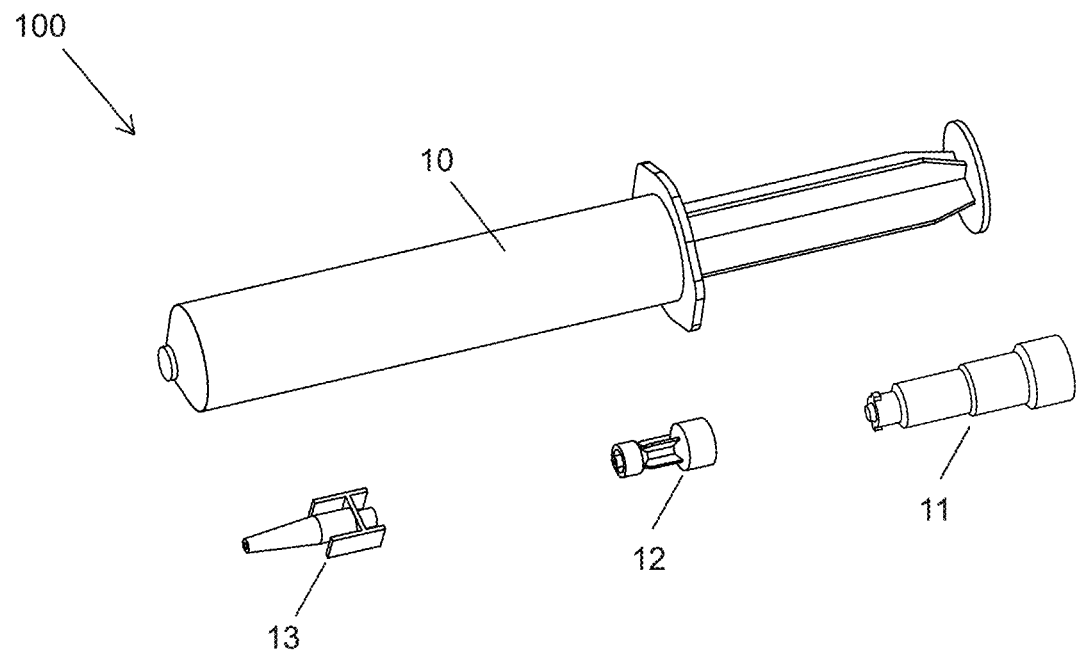
FIG. 1 shows components of a Mitomycin-C Bladder Instillation Syringe Kit, according to an embodiment of the invention.

Although claimed subject matter will be described in terms of certain embodiments, other embodiments, including embodiments that do not provide all of the benefits and features set forth herein, are also within the scope of this disclosure. Various structural, logical, and process step changes may be made without departing from the scope of the disclosure.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all steps, device components, and compositions of matter described herein in the text and figures of this disclosure, including all such items individually and in all combinations. Any formulation, device, and kit, may comprise or consist of the described components, and may comprise or consist of any concentration or weight/volume ratio that is described herein, including any upper or lower value, and all values there between, as described in more detail below.

Mitomycin-C(MMC) is an antineoplastic chemotherapy drug typically used to treat a variety of cancers. MMC degrades in both acidic and alkaline environments. At an acidic pH MMC degrades to 1-hydroxy-2, 7-diaminomitosanes and at basic pH it is hydrolyzed to 7-hydroxymitosane, both of which are considered inactive forms, thereby decreasing efficacy. MMC demonstrates the greatest stability when stored at a pH of 7.0-8.0; however, a 5 mg/mL solution in water has a pH of 6.0-7.5, inclusive, and including all numbers and ranges of pH values there between to the first decimal point, and a saturated solution can have a pH of 5.0-9.0, inclusive, and including all numbers and ranges of pH values there between to the first decimal point. Therefore, it is difficult to maintain the optimal pH of MMC for stability in aqueous solutions.

Intravesical Mitomycin C therapy is used to treat superficial bladder cancer. The degradation of MMC at acidic pH also negatively affects the treatment of patients with bladder cancer as the average pH of urine in the bladder is generally from 5.0 and 6.0 (e.g., approximately 5.0 or approximately 6.0). Current standard of practice amongst urologists and oncologists is to pre-treat the patient in an attempt to alkalinize the urine, however this may result in overshooting the ideal pH range if the urine pH exceeds 8.0. In vitro incubation of MMC in urine demonstrated a 44% decrease in MMC concentrations after 2 hours at pH 5, as compared to less than 4% loss at pH 7. Therefore, acidic degradation accounted for more than one half of the drug loss at low pH.

The formulation described herein provides a readily injectable solution of buffered MMC in propylene glycol that maintains a pH between 7.0 and 8.0 when stressed and instilled into acidic solutions (pH from 4.0 to 6.0 such as a pH of 5.0) and is stable (e.g., less than 10% degradation) when stored at 2-8° C. for greater than 134 days. In a specific embodiment, the buffered MMC in propylene glycol maintains a pH between 7.0 and 7.8 when stressed and instilled into acidic solutions (pH of 5.0) with the disclosed stability benefits. The pH range includes all values to the 0.01 and ranges in between.

In certain embodiments, the formulation may comprise from 0.9 mg/mL to 1.2 mg/mL mitomycin-C USP, which is equivalent to 0.09% to 0.12% (e.g., 0.1%) weight/volume (w/v), 300 mg/mL to 550 mg/mL propylene glycol USP, which is equivalent to 30% to 55% w/v (e.g., 50%), and 0.1 mg/mL to 10 mg/mL sodium phosphate buffer, which is equivalent to 0.01% to 1.0% w/v (e.g., 0.043%). The phosphate buffer may comprise a combination of sodium phosphate dibasic heptahydrate USP and sodium phosphate monobasic anhydrous USP. The concentration range for the sodium phosphate dibasic heptahydrate USP is approximately from 0.0862 mg/mL to 8.87 mg/mL (0.00862% to 0.887% w/v) and the concentration range for the sodium phosphate monobasic anhydrous USP is approximately from 0.0138 mg/mL to 1.42 mg/mL (0.00138% to 0.142% w/v) in sterile water for injection. Alternatively, sterile water for irrigation USP can be used. The disclosed ranges include all values to the 0.01% and ranges in between. Internal research showed that 50% w/v propylene glycol produces the greatest stability of MMC while maintaining dissolution of buffer salts in the solution without precipitation. An approximately 50% propylene glycol 50% buffer formulation allows for both aqueous solubility and organic solubility, which can provide a high enough concentration of organic solvent to keep MMC stable while allowing hydrophilic salts to not precipitate.

A 0.05% to 0.15% (e.g., 0.09%) sodium phosphate buffer was chosen in one example to avoid precipitation of buffer salts at higher concentrations, while maintaining the ability of the drug product to maintain a pH of 7.0-8.0 when injected into acidic solutions, such as urine and when stored at 2-8° C. for at least 134 days.

40-100% glycol is generally stable; however, the pH must also be stable (meaning it does not detectably change), and remain stable when instilled into the bladder because a decreased re-occurrence of bladder cancer has been shown with urinary pH greater than 5.5.

Buffered admixtures of MMC were shown to be stable at 5° C. for 120 days or more. Up to 7 days of stability in buffered solutions also has been shown.

The solubility of MMC at room temperature prepared in water and various other aqueous milieu is approximately 0.9 mg/mL (see Francoeur et al—available at doi: 10.1097/00061198-199908000-00005; Georgopoulos et al—available at doi: 10.1097/00061198-200202000-00004; Gandhi et al—available at doi: 10.1016/j.tca.2012.07.014, which are incorporated by reference in their entirety. Nonetheless, in certain bladder cancer patients, urology surgeons typically utilize MMC preparations in concentrations ≥1 mg/mL, which can supersede its solubility threshold.

It was previously found to be impossible to create a 1 mg/mL solution from the manufactured MMC vial without visual crystalline precipitate in the vial, raising concerns that concentrations of MMC are often prepared, unintentionally, without prior solubilization, which may have adverse practical implications for urologists treating patients with bladder cancer.

3.7% sodium phosphate buffer in 30% propylene glycol solution was used in a particular example. This was calculated on the basis that 3.7% sodium phosphate buffer would provide enough buffer capacity to maintain the pH throughout the drug shelf life, as well as in the bladder, with 30% glycol being a compromise between stability and solubility. This solution formed a precipitate within hours of being stored at 2-8° C. in the final device.

Next, we performed testing of various buffering concentrations and determined a decreased sodium phosphate buffer of 2.1% in 30% propylene glycol solution would increase solubility and prevent precipitation. When we performed a production batch of MMC, however, this also resulted in precipitation despite initially resulting in a dissolved solution.

Finally, we increased the percent of propylene glycol to 50% using sodium phosphate buffer 0.043%. This allowed for increased solubility of MMC in the minimum concentration of buffering salts. This change maintained product stability for 134 days at 2-8° C., while maintaining pH above 7.0 when stressed in pH 5.0 liquid simulating the product being added to acidic urine. Use of a buffer to maintain the pH in an optimal range for treatment makes embodiments of the disclosed formulation the more physiologically effective formulation. For example, previous examples, such as those disclosed in U.S. Pat. No. 5,216,011 were mimicked in our lab, and the pH did not remain above 7.0. In this case the pH remained at 5.3. In contrast, the embodiments disclosed herein can be used with urine having a pH of 4.0 to 6.0.

Several aspects of stability were tested. Potency was assayed using a stability indicating method validated as per USP<621> and <1225>. At end of life, sterility of the product was tested via USP<71> and Container Closure Integrity was tested via dye ingress. The pH of the solution was measured at end of life using the USP<791> method. Embodiments of the formulation disclosed herein met or exceeded each of these stability standards.

In addition to developing a unique, stable formulation for MMC bladder instillation, a kit and method for dispensing were developed. One of the challenges handling MMC is meeting the USP<800> hazardous compounding regulations. In particular, prior to administration, vials of MMC require both fluid reconstitution and drawing up of the required dose into a syringe. Both of these tasks are considered compounding per USP<797> and USP<800> guidelines. The necessary facilities and equipment required to meet these guidelines are well beyond what most clinics and surgery centers will have. Even many hospitals, in particular smaller hospitals and those without cancer centers, will never be able to justify the enormous capital improvement expense necessary to meet USP<800> requirements within their facility. The invention described herein is a pre-filled, unit-dose syringe kit appropriate for bladder instillation of MMC that does not require compounding and brings the end-user (e.g. clinic, surgery center, or hospital) into compliance with USP<800>. Drug manufacturing (i.e. compounding) is performed in an FDA registered 503B Outsourcing facility. Utilizing an FDA registered 503B Outsourcing facility to produce pre-filled syringes of MMC for bladder instillation provides an ideal source, since patient names (i.e. prescriptions) are not required, and extended Beyond Use Dating (BUD) is possible.

FIG. 1 shows the components of a Mitomycin-C Bladder Instillation Syringe Kit 100. The kit comprises a syringe 10 filled with MMC and a closed system transfer device (CSTD) 11, which provides a means to handle and administer MMC, a chemotherapy drug, in accordance with USP<800> hazardous compounding regulations. The Syringe Kit shown in FIG. 1 consists of a PhaSeal™ CSTD Injector Luer Lock (BD PhaSeal™ Part Number N35) 11 and a PhaSeal™ CSTD Connector Luer Lock (BD PhaSeal™ Part Number C45) 12. Optionally, a catheter tip connector 13 may be included with Syringe Kit 100.

Figure 2:
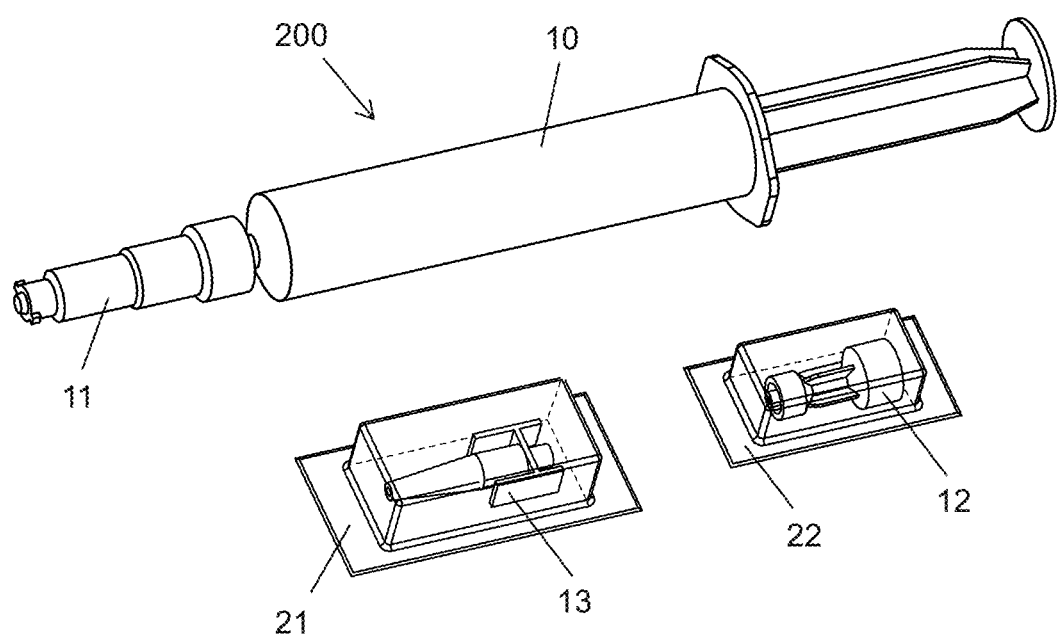
FIG. 2 shows a Mitomycin-C bladder instillation syringe assembly including closed system transfer device and accessories, according to an embodiment.

FIG. 2 shows Syringe Assembly 200, which comprises CSTD 11 connected to syringe 10. Alternatively, these two components could be fashioned as one piece (i.e. a combined syringe and CSTD). FIG. 2 also shows catheter tip connector 13 in sterile packaging 21, as well as connector luer lock 12 in sterile packaging 22. The final kit utilized by end-users (i.e. customers) comprises Syringe Assembly 200, sterile packaged catheter tip 21, and sterile packaged connector luer lock 22.

Figure 3:
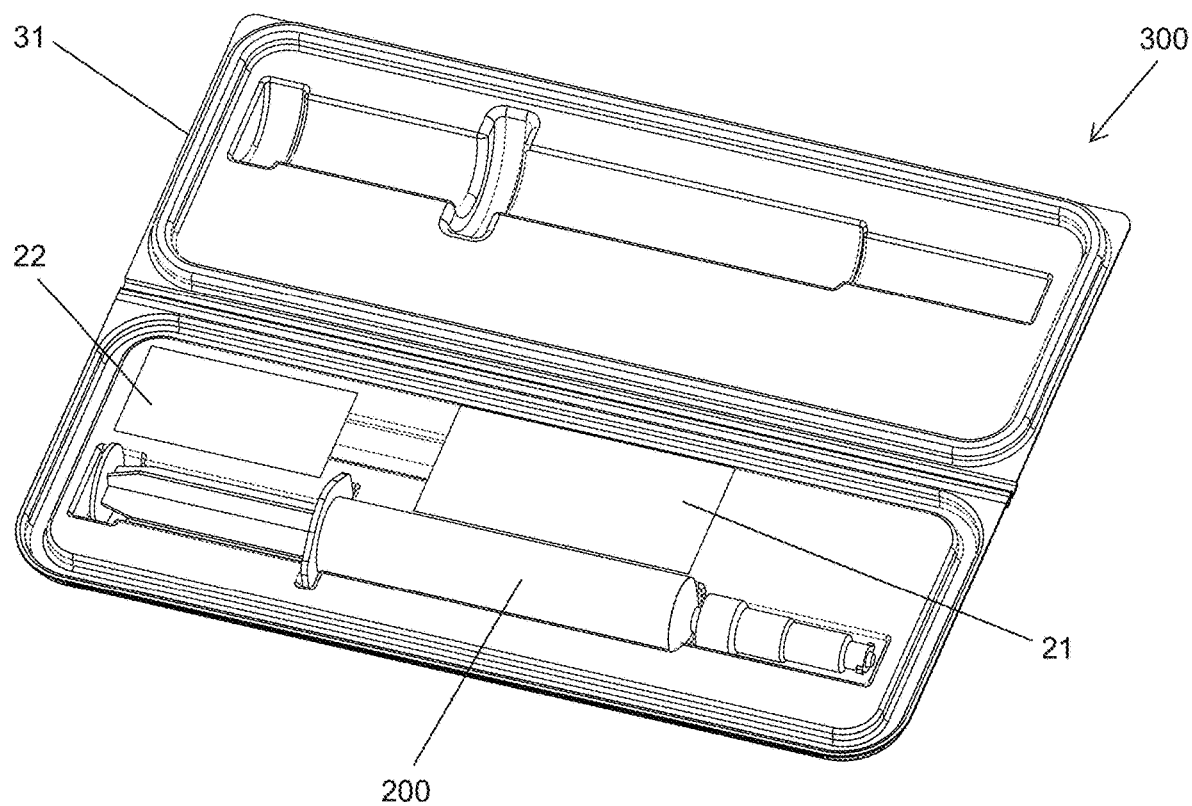
FIG. 3 shows a Mitomycin-C syringe kit packaged in a molded container.
Figure 4:
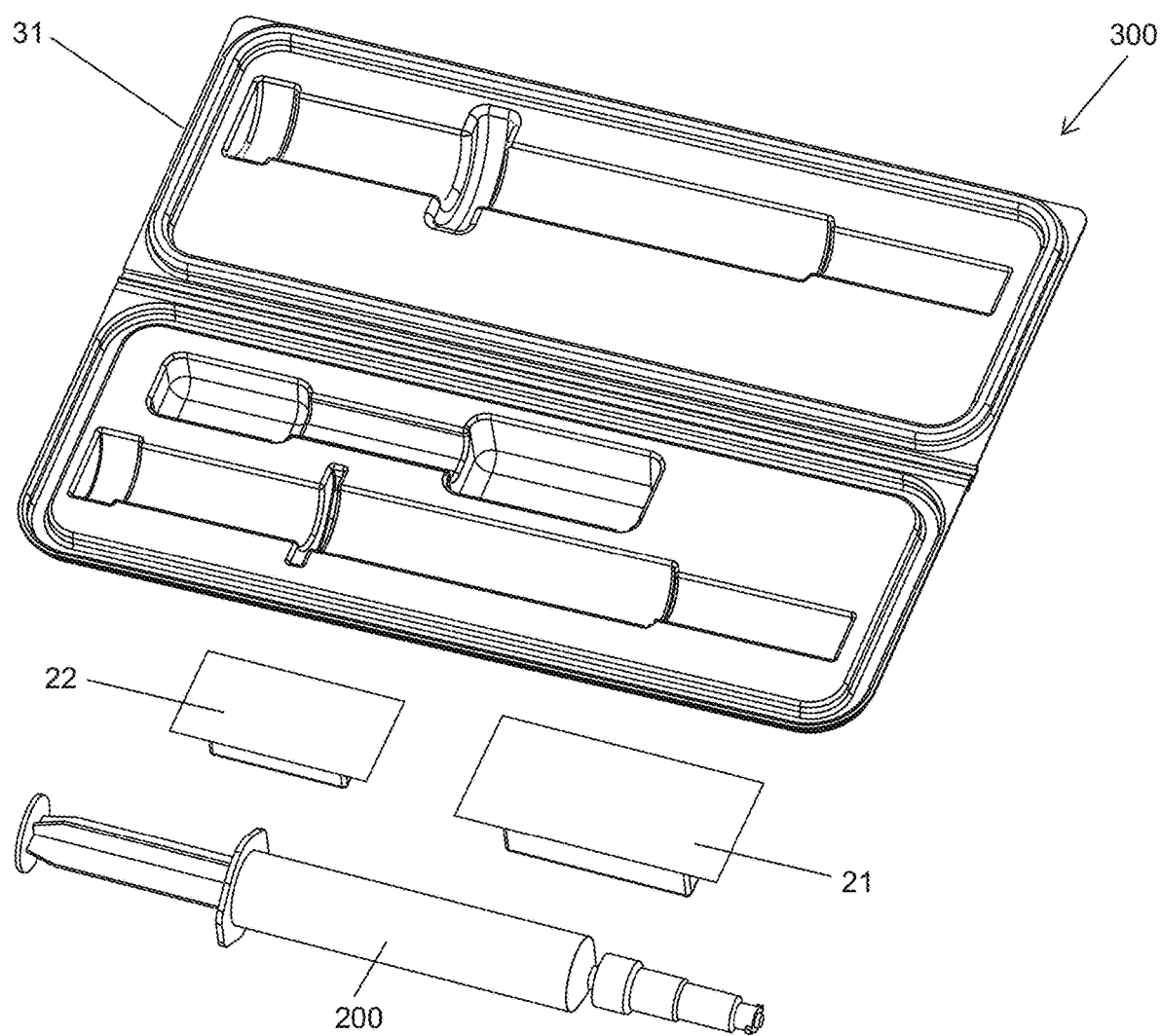
FIG. 4 shows an exploded view of the Mitomycin-C syringe kit shown in FIG. 3.

FIG. 3 shows a Syringe Kit 300, which comprises Syringe Assembly 200, sterile packaged catheter tip 21, sterile packaged connector luer lock 22, and molded container 31. The molded container 31 provides a convenient packaging for the entire MMC Syringe Kit. FIG. 4 shows an exploded view of Syringe Kit 300.

Alternatively, the CSTD could be any closed system transfer device that connects to the end of a syringe, or any combined syringe and closed system transfer device.

Alternatively, Gemcitabine, another chemotherapy medication often instilled into a bladder, can be used in place of Mitomycin-C in the pre-filled syringe kit. In this case, a Syringe Assembly 200 is filled with Gemcitabine in a 503B Outsourcing facility, which includes a CSTD 11 attached to the end of the syringe 10 (or pre-attached to the syringe), and the combination is dispensed to the hospital, surgery center, or clinic with connector luer lock 12 and catheter tip connector 13 (or equivalent accessories if the CSTD system is other than PhaSeal™).

Accordingly, it is to be understood that the embodiments of the invention herein described are merely illustrative of the application of the principles of the invention. Reference herein to details of the illustrated embodiments is not intended to limit the scope of the claims, which themselves recite those features regarded as part of the invention.

What is claimed is:

1. A Mitomycin-C formulation comprising:
   0.9 mg/mL to 1.2 mg/mL Mitomycin-C;
   300 mg/mL to 550 mg/mL propylene glycol;
   0.1 mg/mL to 10 mg/mL sodium phosphate buffer;
   and water.

2. The Mitomycin-C formulation of claim 1, wherein the sodium phosphate buffer comprises a combination of sodium phosphate dibasic heptahydrate and sodium phosphate monobasic anhydrous.

3. The Mitomycin-C formulation of claim 2, wherein the sodium phosphate dibasic heptahydrate has a concentration of 0.0862 mg/mL to 8.87 mg/mL.

4. The Mitomycin-C formulation of claim 2, wherein the sodium phosphate monobasic anhydrous has a concentration of 0.0138 mg/mL to 1.42 mg/mL.

5. The Mitomycin-C formulation of claim 2, wherein the sodium phosphate dibasic heptahydrate has a concentration of 0.0862 mg/mL to 8.87 mg/mL and the sodium phosphate monobasic anhydrous has a concentration of 0.0138 mg/mL to 1.42 mg/mL.

6. A bladder instillation syringe kit comprising:
   a syringe;
   a closed system transfer device connected to the syringe; and
   a Mitomycin-C formulation comprising:
      0.9 mg/mL to 1.2 mg/mL Mitomycin-C;
      300 mg/mL to 550 mg/mL propylene glycol;
      0.1 mg/mL to 10 mg/mL sodium phosphate buffer; and
      water.

7. The bladder instillation syringe kit of claim 6, wherein in the Mitomycin-C formulation, wherein the sodium phosphate buffer comprises a combination of sodium phosphate dibasic heptahydrate and sodium phosphate monobasic anhydrous.

8. The bladder instillation syringe kit of claim 7, wherein the sodium phosphate dibasic heptahydrate has a concentration of 0.0862 mg/mL to 8.87 mg/mL.

9. The bladder instillation syringe kit of claim 7, wherein the sodium phosphate monobasic anhydrous has a concentration of 0.0138 mg/mL to 1.42 mg/mL.

10. The bladder instillation syringe kit of claim 7, wherein the sodium phosphate dibasic heptahydrate has a concentration of 0.0862 mg/mL to 8.87 mg/mL and the sodium phosphate monobasic anhydrous has a concentration of 0.0138 mg/mL to 1.42 mg/mL.

11. A bladder instillation syringe kit comprising:
    a syringe;
    a closed system transfer device connected to the syringe; and
    a Mitomycin-C formulation comprising;
       0.9 mg/mL to 1.2 mg/mL Mitomycin-C;
       300 mq/mL to 550 mq/mL propylene glycol;
       0.1 mq/mL to 10 mg/mL sodium phosphate buffer; and
       water, wherein the bladder instillation syringe kit is produced in a 503B Outsourcing Facility.

* * * * *